United States Patent [19]

Duboff

[11] Patent Number: 4,796,182

[45] Date of Patent: Jan. 3, 1989

[54] DIET MONITOR AND DISPLAY DEVICE

[76] Inventor: Gary Duboff, 10066 Bay Harbor Ter., Bay Harbor Island, Fla. 33154

[21] Appl. No.: 941,629

[22] Filed: Dec. 15, 1986

[51] Int. Cl.[4] ............................................. G06F 15/42
[52] U.S. Cl. ............................................... 364/413.29
[58] Field of Search ................................. 364/413, 415

[56] References Cited

U.S. PATENT DOCUMENTS

| | | | |
|---|---|---|---|
| 4,321,674 | 3/1982 | Krames | 364/413 |
| 4,575,804 | 3/1986 | Ratcliff | 364/413 X |
| 4,686,624 | 8/1987 | Blum | 364/415 |

OTHER PUBLICATIONS

Moran, "Electronic Diet Controller", published in Computer Design, Aug. 1977, pp. 116–118.

Primary Examiner—Jerry Smith
Assistant Examiner—Steven G. Kibby
Attorney, Agent, or Firm—Wallenstein, Wagner Hattis & Strampel Ltd.

[57] ABSTRACT

An electronic device for displaying preset amounts of food categories allowable in a daily diet, for permitting a digital entry representative of food consumed, and for subtracting that entry from the preset amount and displaying the result.

14 Claims, 1 Drawing Sheet

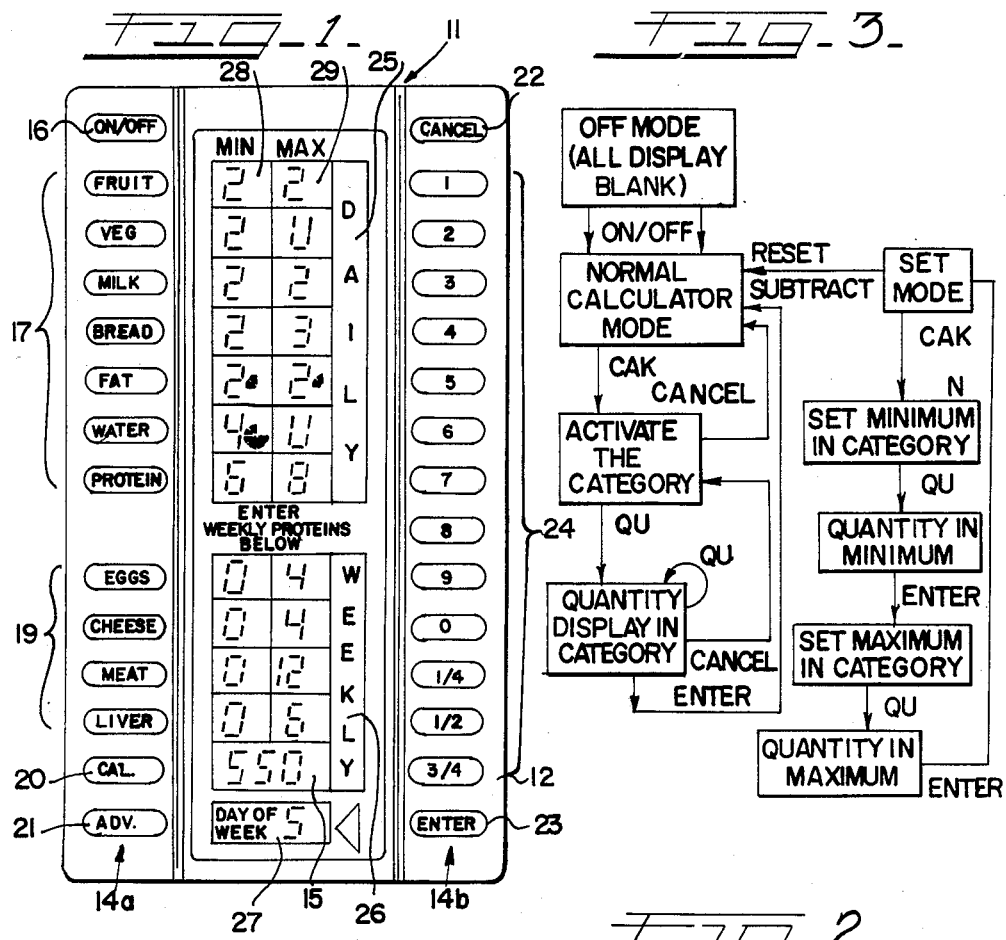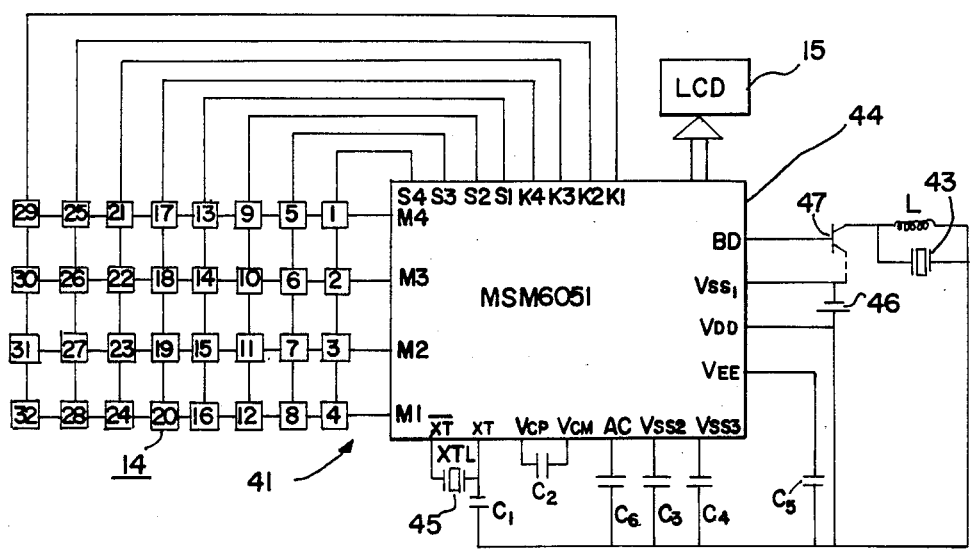

DIET MONITOR AND DISPLAY DEVICE

DESCRIPTION

FIELD OF THE INVENTION

The invention relates to electronic devices for monitoring a diet, as for example an exchange-type diet, and for displaying the minimum and maximum amounts of various food categories to be consumed by the dieter during a given day or week.

BACKGROUND OF THE INVENTION

Dieters must generally record either the amounts of foods they have consumed or the caloric content of those foods. One popular type of diet is the so-called "exchange" diet. The exchange diet limits the dieter to a preselected number of units of different food categories during a given day or week.

For example, a hypothetical exchange diet may limit the dieter to two units of fruit, unlimited units of vegetables, two units of milk, two units of bread, three units of fat, an unlimited amount of water, and eight units of protein. Typically, the dieter must also consume a minimum number of units from each of these categories every day. During a given week, the dieter may be limited to four units of eggs, four units of cheese, twelve units of meat, and six units of liver. These weekly limited items are proteins. Thus, when a dieter consumes, under this hypothetical exchange diet, two egg units at the first meal of a diet week, he has reduced his permissible remaining weekly consumption of eggs to two units. In addition, he has reduced his permissible daily consumption of protein to six units.

Maintaining a manual record of the units consumed in each category can be tedious and error-prone. It was thus believed desirable to invent a diet monitor for electronically tracking the dieter's progress.

SUMMARY OF THE INVENTION

The present invention is a device which includes electronic processing circuitry for indicating minimum and maximum daily and weekly consumption of a variety of foods. The invention comprises means for visually displaying selected food categories; means for visually indicating the minimum and maximum amounts of selected food categories consumable daily; switch means for activating entry of a food category into the electronic processing circuitry; means for actuating entry of the amounts consumed in those selected food categories, and for subtraction of those amounts from the daily allowable amounts; and means for digitally displaying the remaining amount of each food category consumable during the dieting day. The device also includes means for digitally displaying the maximum allowable weekly consumption of certain selected food categories; means for indicating that the allowable daily consumption of a food category has been exceeded; and means for indicating that the allowable weekly consumption of a food category has been exceeded.

The device may also include means for displaying the amount of selected food categories allowable on a weekly basis. In another embodiment, means are provided for displaying the daily permissible consumption of certain food categories, and for displaying the remaining allowable amount from both daily and weekly maximum amounts. Finally, the device may include a display for indicating minimum and maximum quantities of daily allowable amounts of food categories.

Accordingly, an object of the invention is to provide a diet monitor which eliminates the need for dieters to keep manual records of their exchange diets. Another object of the invention is a diet monitor which enables the user to program the minimum and maximum amounts of foods consumable under any exchange diet. Another object of the invention is a means for displaying the minimum and maximum amounts of food that may be consumed daily or weekly under a given exchange diet.

Yet another object of the invention is a diet monitor which coordinates the weekly and daily subtraction of food categories when a weekly-limited item corresponds to a food category that has daily consumption limits.

BRIEF DESCRIPTION OF THE DRAWING

FIG. 1 is a plan view of the inventive device showing typical digital displays;

FIG. 2 is block diagram of the electronic circuitry of the device of FIG. 1; and FIG. 3 is a flow diagram showing the programming steps incorporated in the device to provide the indicated displays.

DESCRIPTION OF THE PREFERRED EMBODIMENT

FIG. 1 is a plan view of the calculator 11 in accordance with the invention. Calculator 11 is housed in a substantially rectangular housing or case 12. The front or display face 14 of the case 12 includes a vertically and centrally disposed liquid crystal display (LCD) 15 and a number of push buttons or keys arranged in two spaced vertical rows 14A and 14B, which straddle the display 15. The left hand row 14A starting from the top includes the ON-OFF button or key 16, a group of seven buttons or keys generally labeled as 17 for selectively entering different daily allowable food categories, a group of four buttons or keys 19 for selectively entering weekly allowable food categories, and a bottom button 20 for entering calorie input. A recessed switch pad 21, labeled ADVANCE, is recessed in housing 12 and can be activated typically by a narrow sharp object such as the user's fingernail. The advance pad 21 advances the day of the week entry from 1 to 2 to 3, and so on until it reaches 7. Then, it advances the day of the week from 7 to 1, and repeats. Pad 21 is recessed to avoid its accidental actuation.

The right-hand row 14B contains a top recessed pad 22, labeled CANCEL, similar to advance pad 19. Depressing pad 22 cancels any desired entry such as an entry made by accidental actuation of a numerical key. Numerical integer or fraction entry keys or buttons 1-9, 0, ¼, ½ and ¾, which are generally labeled 24, and a bottom ENTER key 23, are positioned in a row beneath pad 22.

The LCD display 15 is of a suitable known functional design, and comprises two vertical columns 28 and 29 indicating a minimum and maximum numerical amount opposite each of the food category rows. Thus, each food category has a position for minimum and maximum numerical entries. The upper group 25 of food categories, labeled DAILY, includes a display of food quantity or amount allowable on a daily basis to a user. The lower group 26 of food categories, labeled WEEKLY, includes a display of food quantity or amount allowable on a weekly basis to the user. The calories display, labeled CAL, shows a preset selected amount of additional calories allowable on a weekly basis to the user. The bottom display 27 shows the day of the week, indicated selectively as a number from 1 to 7.

A week reset switch (not shown in FIG. 1) is positioned at the back or rear side of the case 12. Depressing this switch allows the user to instantly reset the calculator to day 1. When the calculator is set to day 1 in this manner, the original default values or the user-set values will reappear on the LCD display 15 in their respective positions.

Depressing program set/lock switch (also not shown in FIG. 1) positioned on the back face of case 12 allows the user to enter a set mode, which permits entry and setting of user-selected numercial values in each of the food categories, as will be explained.

As indicated above, there are seven daily food categories in group 25, each with specific minimum and maximum diet quantity values. These are fruit, vegetable, milk, bread, fat, water and protein, as labeled on the keys 17 of FIG. 1.

There are four weekly limited protein foods in group 26, each shown with no minimum requirement. These are eggs, cheese, meat and liver. The weekly or limited protein group 26 has a specific maximum weekly allowable quantity. The other weekly category, calories, has only a specific maximum allowable quantity.

FIG. 2 shows a block diagram of the circuitry 41 of the calculator 11 of FIG. 1. The circuitry 41 includes a microprocessor chip 44 designated as a MSM6051, the associated crystal 45, suitable capacitors C1-C6, a battery source 46, a transistor 47 connecting to a parallel circuit of the inductance L and audio signal source 43. Chip 44 is programmed to provide a quantity enter and quantity subtract function, and also provides an audio signal as at 43 upon entry of a food amount above that preset as being allowable. The connections for the push buttons or keys 14A and 14B are arranged in a known rectangular matrix configuration to provide selected input entry to the microprocessor 44. Note that the numerical inputs shown in the vertical row 14B of the display of FIG. 1, do not necessarily correspond to the numbers in the matrix 14 of FIG. 2. For example connection number 1 in the matrix of FIG. 2 represents the entry for the day of the week reset switch of FIG. 1; and, connection number 18 represents the enable switch for the reset mode.

FIG. 3 shows an operation flow chart of the circuitry 41 of FIG. 2 and will now be described. Upon turning the calculator 11 ON, the calculator enters its normal mode. As a specific example, assume the user is entering the consumption of a vegetable. Upon actuation of the particular category activation key (CAK) labeled VEG in FIG. 1, the circuitry 41 activates that category. Next, one of quantity keys labeled 1-9 (QU) is activated dependent on the amount of the vegetable category consumed. Next the enter key is depressed (activated), and the amount of vegetable consumed is subtracted from the preset amount which appeared on the display 15.

More generally and as indicated in the flow chart of FIG. 3, upon consuming a specific food, user does the following:

A. Presses the key of the corresponding food group. This actuates both the minimum and maximum LCD's of that category to a flashing state, awaiting entry of the specific amount of food being consumed.

B. Presses the number digit representing the amount of food being consumed. A single digit or single digit plus a fraction may be pressed, and that amount now appears in a non-flashing state on either the minimum or maximum display of the respective LCD. The other display of the respective LCD goes blank and awaits entry.

C. Presses ENTER. A subtraction is made in both minimum and maximum LCDs and new digits appear indicating the amount of that food category allowable during the balance of the day and the balance of week.

The CANCEL key can be activated to cancel any proposed entry, either in the normal or set mode, before it is entered.

On activation of the ON/OFF key, the data display is turned on and off. The data display remains unchanged, and the calculator remains in this normal calculator mode. Should the unit be on for five minutes, the display is turned out and the keys are locked out except the ON/OFF key.

As mentioned, the two set mode switches number 1 and 18 indicated in FIG. 2 are positioned in the back of the case of FIG. 1 to set the day of the week indication in the display. Switch 1 when activated enables the set mode to reset the day of the week to day 1. Switch 18, when activated, enables the resetting of the minimum and maximum quantities in the selected category.

As shown in the flow chart of FIG. 3, when the set mode switch is activated, the program enters the set mode, and the day of week display starts flashing as three linear segments. If any of the upper category group 17 keys are actuated, that particular display's figures flash. A preselect quantity or amount is selected by activating (pressing) one of integer or fractional numeric keys in column 14B. The minimum number is entered by activating the enter key; at this time the minimum number display stops flashing. The maximum number display then begins to flash with the previously user-set minimum number. Next the maximum desired amount is selected by activating one of numeric keys in column 14B. The enter key is then activated to enter the maximum amount, and the maximum amount display stops flashing. When a fractional amount, $\frac{1}{4}$, $\frac{1}{2}$ or $\frac{3}{4}$, is entered, the fractional amount is added to the number and this appears with the number as a respective portion of a pie chart on the display.

If any other categories are to be reset, the procedure is repeated. They reset to either the values initially preset in the unit or to values (within selected ranges) which are set by the user.

When the day of the week is advanced, the day digit is increased by one, and the minimum and maximum amounts of the daily categories are reset to the preselected setting. When the day of the week is reset from day 7 to day 1, both the upper (daily) and lower (weekly) groups will reset to the preselected amounts. At least one subtraction entry must be made from the daily or weekly amounts before the day can be advanced. The weekly reset key at the back of the case will reset the day of week to "1" and the LCD display to the preselected amounts. The U or unlimited quantity display is set by entering "0" three times, i.e. pressing the "0" key three times. The set mode switch is actuated a second time to return the unit to its normal calculator mode.

In the normal calculator mode, when a person consumes one of the four weekly "limited" proteins, the amount is entered in the weekly protein section, and this amount is also subtracted from the preset protein amount displayed in the daily group. For example, the egg key in the weekly category is depressed, the protein display in the daily category also starts flashing, because eggs are a protein. Upon entry of a numerical amount, this amount is subtracted from both the daily protein and weekly egg totals. If the protein display is "0", the weekly category keys 19 are locked out.

If an amount number key 24 is depressed, and the value of that key exceeds the allowable entry, a single beep will occur. A "0" entry is not accepted. When the category values are "0", that category key is locked out. If the protein display is "0", this locks out the lower four category keys group 26.

Under certain circumstances, the calculator will respond with a double beep. For example, assume the calculator is in the normal mode and the displayed minimum and maximum values for the daily milk allowance set at "2". If the user depresses the "milk" button, the numerals "2" under both the minimum and maximum columns will begin flashing. If the user depressed the "2" numeric key and then the "enter" button, the normal subtraction would be effected by the calculator and the milk row would show "0" in both the MIN and MAX columns. However, if the user instead attempted to enter 2½ units by first depressing the "2" numeric key and then the "½" numeric key, the calculator would respond to this attempt at excessive consumption by beeping twice and by indicating an error by a flashing "E" under the MIN column of the milk row.

The calculator is not programmed to add fractions. If 3 units of fat remain for daily consumption in both the minimum and maximum columns, and the user attempted to enter 2 units of fat by first pressing the "1" numeric key and then by twice depressing the "½" numeric key, the calculator would beep twice and an error would be indicated by a flashing "E" in the MIN column of the FAT row.

A double beep will also occur if the user inadvertently exceeds the allowable units by first pressing an integer numeric key, then pressing a fractional numeric key, and then pressing another integer unit. For example, when the user depresses the "1" numeric key, then the "½" numeric key, and then again depresses the "1" numeric key, the calculator interprets such an entry as corresponding to the entry of 11½ units. Assume that the protein MIN column is at 6 and the protein MAX column is at 8. By depressing the protein key, the "6" and "8" will begin flashing. If the operator enters 1½ units of protein by first depressing the "1" and then the "½" numeric keys, the calculator will not respond adversely because 4½ minimum units of protein and 6½ maximum units of protein remain. However, if before depressing the "enter" button the user now again inadvertently depresses the "1" numeric key a double beep will be heard. The calculator deems the number of units attempted to have been entered as 11½, which exceeds the maximum permissible proteins for that day.

A double beep will occur when the user attempts to enter a unit consumption which simultaneously exceeds both a weekly and daily protein. Assume that the maximum permissible weekly egg allotment is 4 and that the maximum permissible daily protein allotment is 8 under a given exchange diet. If one depresses the "eggs" button, and then attempts to enter 10 eggs, a double beep will be sounded and a flashing "E" will appear under the maximum columns for both "protein" and "eggs."

Finally, a double beep will be heard if one attempts to enter a weekly protein when no additional daily proteins may be consumed. For example, if "0" appears in the MAX column of the daily "protein" row, the mere depressing of the "meat" button in the weekly protein category, even if additional units of meat may be consumed by that dieter during the week, will result in a double beep and a flashing "E" in the protein MAX column.

Whenever a double beep occurs, the user can return the calculator to the normal mode by depressing the cancel button once or twice.

While the invention has been particularly shown and described with reference to a preferred embodiment thereof, it will be understood by those skilled in the art that various changes in form and details may be made therein without departing from the spirit and scope of the invention.

I claim:

1. A display device responsive to electronic processing means for visually presenting digital data representative of a dietary plan comprising in combination,
   (a) means for digitally displaying respective minimum and maximum allowable daily consumption in selected food categories by said plan,
   (b) means for digitally displaying respective minimum and maximum allowable weekly consumption in selected food categories by said plan,
   (c) dedicated manually operable switch means for selecting one food category among said selected food categories,
   (d) meanually operable switch means for activating a digital amount representative of an amount of food consumed in said food category,
   (e) switch means for commanding entry of said digital amount of said food category to said processing means for processing and subtraction from the displayed minimum and maximum amounts, and
   (f) means for storing the remaining allowable daily and weekly amounts in each of said selected food categories.

2. A device as in claim 1 further including means to provide an auditory signal if a digital amount commanded to be entered is a higher amount than the maximum displayed amount.

3. A device as in claim 2 further including:
   (a) means for indicating that the maximum allowable daily consumption in a food category has been exceeded, and
   (b) means for indicating that the maximum allowable weekly consumption in a food category has been exceeded.

4. A device as in claim 3 wherein means are included for displaying the remaining maximum daily allowable consumption from a previously selected daily maximum amount as well as for displaying the remaining maximum weekly allowable consumption from a previously selected weekly maximum amount.

5. A device as in claim 3 further including means for displaying an allowable weekly consumption in selected weekly categories of food containing protein, and means for displaying an allowable daily consumption in a total daily proteing category, and further comprising means for subtracting an amount from the allowable daily protein displayed concurrently with the subtraction of an equal amount from the display of said allowable consumption from any of said weekly categories of food containing protein.

6. A device as in claim 1 further including audio means for providing a signal comprising a single reep which is indicative of the non-acceptance of a digital amount.

7. A device as in claim 6 wherein said audio means provides a signal comprising a double beep which is indicative of the non-acceptance of an attempt to enter a digital amount representative of the overconsumption of a food category.

8. A device as in claim 7 wherein said device further comprises display means that provides a visual character as said double beep is effected.

9. A device as in claim 7 wherein said device further comprises audio means that provides a double beep representative of the non-acceptance of an attempt to add digital amounts before substraction occurs.

10. A device including electronic processing means for indicating allowable daily consumption in a variety of categories of foods comprising in combination:
 (a) means for visually displaying the minimum and maximum allowable daily consumption in selected food categories,
 (b) switch means for activating entry of a food category into said electronic processing means,
 (c) means for actuating entry of the amount of consumption in selected food categories and subtraction thereof from said consumption allowable daily, and
 (d) means for digitally displaying the remaining minimum and maximum amounts in said food categories allowable daily, and
 (e) means for storing the remaining allowable daily amounts in each of said selected food categories.

11. A device as in claim 10 further including a means to display the day of the week and means for manually activating the device to advance the day of the week.

12. A device as in claim 10 further including means for manually actuating the device to a numerical entry set mode, said numerical entry set mode permitting the user of said device to enter and set minimum and maximum user-selected consumption amounts for each of said food categories.

13. A device as in claim 12 including means for providing an audio signal to indicate a non-allowable proposed numerical entry.

14. A device as in claim 12 further including fractional digit display means in the form of a portion of a pie chart, said fractional digit display means being activated when fractional units of selected food categories are entered during the numerical entry set mode, or when fractional units remain to be consumed.

* * * * *

UNITED STATES PATENT AND TRADEMARK OFFICE
CERTIFICATE OF CORRECTION

PATENT NO. : 4,796,182
DATED : January 3, 1989
INVENTOR(S) : Gary Duboff

It is certified that error appears in the above-identified patent and that said Letters Patent is hereby corrected as shown below:

Column 5, line 2, after "For example," should read --when--.

Column 6, line 32, "meanually" should read --manually--.

Column 6, line 63, "proteing" should read --protein--.

Column 7, line 2, "reep" should read --beep--.

Signed and Sealed this

Second Day of May, 1989

Attest:

DONALD J. QUIGG

*Attesting Officer*

*Commissioner of Patents and Trademarks*